United States Patent [19]

Tepper

[11] Patent Number: 5,052,409

[45] Date of Patent: Oct. 1, 1991

[54] ORAL APPLIANCE FOR TONGUE THRUST CORRECTION

[76] Inventor: Harry W. Tepper, 535 Ocean Ave. #2B, Santa Monica, Calif. 90402

[21] Appl. No.: 608,979

[22] Filed: Oct. 31, 1990

Related U.S. Application Data

[62] Division of Ser. No. 348,561, May 8, 1989, Pat. No. 4,986,283.

[51] Int. Cl.$^5$ ............................................. A61C 5/14
[52] U.S. Cl. ...................................... 128/859; 128/860
[58] Field of Search ............... 128/859, 860, 861, 862; 433/5, 6

[56] References Cited

U.S. PATENT DOCUMENTS

| | | | |
|---|---|---|---|
| 2,037,079 | 4/1936 | Locke | 128/859 |
| 2,844,142 | 7/1958 | Gibbons | 128/860 |
| 3,219,033 | 11/1965 | Wallshein | 128/860 |
| 3,259,129 | 7/1966 | Tepper | 128/860 |
| 3,277,892 | 10/1966 | Tepper | 128/860 |
| 3,312,216 | 4/1967 | Wallshein | 128/860 |
| 3,337,958 | 8/1967 | Stifter | 433/5 |
| 3,884,226 | 5/1975 | Tepper | 128/860 |
| 4,299,568 | 11/1981 | Crowley | 433/6 |
| 4,471,771 | 9/1984 | Brown | 128/859 |
| 4,901,737 | 2/1990 | Toone | 128/859 |

Primary Examiner—Robert A. Hafer
Assistant Examiner—Michael Brown
Attorney, Agent, or Firm—Spensley Horn Jubas & Lubitz

[57] ABSTRACT

An oral appliance for tongue thrust correction includes a pair of thin wire filament loops pivotally coupled together for limited pivotal movement about an axis. One loop forms a palatal portion and the other loop forms a lingual portion which includes a bridge for spanning the dorsum of the tongue. A spring urges the bridge away from the palatal portion and against the dorsum whereby contact with the dorsum encourages the tongue to a position through the palate and lingual portions and to properly seat on the rugae for maintaining proper proprioceptive sense. The bridge includes means for dispensing a stimulant for increasing the swallowing frequency. The corrective habit established by use of the appliance inhibits snoring and brings about improvement in malocclusion, TMJ and related disorders. An embodiment of the appliance includes a pair of thin flexible filaments which couple the palatal and lingual portions together. The filaments are located on each side of the palatal portion between the anterior and posterior ends thereof and provide both pivotal and translational movement of the lingual portion with respect to the palatal portion. Alternatively the oral appliance includes a single wire filament loop and a bridge coupled to the posterior portion of the loop. The bridge includes a receptacle for receiving a stimulant which is maintained between the palate and the receptacle when the appliance is installed. The wire filament may be severed midway its length and encased in a non-toxic sleeve.

28 Claims, 6 Drawing Sheets

ORAL APPLIANCE FOR TONGUE THRUST CORRECTION

This is a division of application Ser. No. 07/348,561, filed on May 8, 1989, now U.S. Pat. No. 4,986,283.

BACKGROUND OF THE INVENTION

The present invention relates to a simple yet very effective apparatus for correcting tongue thrust or facial oral muscular dysfunction. More specifically, the appliance encourages the tongue to a position through lingual and palatal portions of the appliance to seat on the rugae for maintaining proper proprioceptive sense.

Facial oral muscular dysfunction or tongue thrust manifests in several severe disorders. Examples of such disorders are snoring and sleep apnea as well as malocclusion and relapse and temporal mandibular syndrome. Snoring and sleep apnea often give rise to both health and social problems. In the severe sense, loud snoring has been known to result in disharmony in spousal relationships ending often times in marriage dissolution. People kept awake by snoring often exhibit diminished work efficiency and failure to be attentive leading to both industrial and driving accidents.

From a health standpoint people who snore can develop an aggravated condition known as sleep apnea which is the interruption of normal breathing during sleep. Failure to oxygenate the brain during episodes of sleep apnea not only interfere with normal brain functioning, but can also result in drowsiness and narcolepsy. The result of narcolepsy during activities such as driving obviously can result in serious injury and even death.

Intensified sleep apnea symptoms known as obstructive sleep apnea, which is caused by rhythmic breathing through the mouth during periods of respiratory congestion, cause the laryngeal pharynx part of the muscular mucosa muscle to swell to the extent that it completely blocks the airway passage. Remedies under this severe condition include a tracheotomy procedure.

Simply stated, snoring involves a displacement of the rest position of the tongue and a breathing disorder such as breathing through the mouth resulting from the abnormal positioning and functioning of the tongue. In the normal position the tongue should be in contact with the rugae, the anatomical folds or wrinkles especially of the mucosa of the anterior palatal region of the mouth. The abnormal position of the tongue leaves a space for the passage of air between the hard palate and the top of the tongue and over the soft palate. The passage of air over the soft palate causes it to vibrate (fibrillation) resulting in the familiar disquieting snoring sound.

Muscular dysfunction is also manifest in malocclusions originating as early as birth where babies develop an anterior or reverse tongue thrust problem due to the forward pushing of the tongue to repel intrusive feeding attempts.

Malocclusions are also related to temporal mandibular joint syndrome commonly known as TMJ and can be directly traced to tongue thrust. Devices to remedy aspects of the foregoing described symptoms have been made. U.S. Patent No. 3,884,226 entitled APPARATUS FOR CORRECTING TONGUE THRUST issued to the inventor of the subject invention is an early attempt to provide tongue thrust correction by means of an appliance having a solid palatal and lingual portion which prevent the tip of the tongue or apex to contact the rugae. As such the aforementioned device failed to provide the enhanced corrective advantages realized by the present invention.

SUMMARY OF THE INVENTION

The present invention solves the above-mentioned problems by providing an oral appliance having a palatal portion having proximal and distal ends; the palatal portion formed of thin wire filament disposed along a lingual gingival surface of the upper teeth; the proximal end being adjacent the anterior teeth and the distal end being adjacent the posterior teeth; a lingual portion comprising a thin wire filament having first and second ends, the lingual portion being pivotally mounted at its first end to the proximal end of the palatal portion for movement about a pivot axis; bridge means supported at the second end substantially spanning the palate for bearing against the dorsum of the tongue; and resilient band means connected laterally across the distal end of the palatal portion for urging the lingual portion away from the palatal portion and the bridge means against the dorsum of the tongue.

Preferably the bridge means of the appliance comprises a thin arched band whose arch substantially conforms to the contour of the dorsum of the tongue.

Preferably the resilient band means biases the bridge means against the dorsum of the tongue sufficiently to cause the anterior part of the tongue to contact the rugae for proper proprioceptive feel.

Preferably the appliance includes absorption means for absorbing and then dispensing liquid stimulant.

In one embodiment of the invention the palatal and lingual portions are linked together by means of thin flexible filaments protruding from respective sides of the palatal portion. The filaments are fixedly secured in the lingual portion while being capable of limited translational movement in the palatal portion. Accordingly, due to the flexibility of the filaments and their movement with respect to the palatal portion, the lingual portion is capable of both pivotal movement about a pivot axis as well as limited translational movement with respect to the palatal portion.

The appliance is comfortable, inexpensive, non-invasive and removable, and when installed, effectively inhibits the onset of snoring and the various degrees of sleep apnea. The appliance attaches simply to selected upper posterior teeth and is smaller, lighter and significantly more effective than a palatal retainer or plate. Uniquely and advantageously, the appliance stimulates correct swallowing action and salivation while the patient is asleep to eliminate the snoring/apnea syndrome. Obstructive sleep apnea is also related to mouth breathing, improper tongue posture and a reduced amount of swallowing. This problem is related primarily to the depletion of $CO_2$ which heavy snorers present. Heavy snorers in their breathing produce a "bellows effect" by depleting the $CO_2$ in the lungs and in the blood stream.

The deficiency of $CO_2$ causes an interruption in the normal breathing process until the body regenerates a sufficient amount to again initiate breathing. The swallowing frequency as encouraged by the appliance interrupts the cycle of bellows breathing before it gets to the apnea stage. The improvement in the swallowing frequency is directly related to improvement in the generation of $CO_2$.

The swallowing frequency may be increased as a result of the existence of a bolus of food which is a semi-liquid quantity of food produced by chewing. The presence of the bolus of food encourages the salivatory, masticatory and swallowing centers of the brain with the corresponding activity in the mouth. Use of the appliance simulates the existence of a bolus of food in the mouth to further improve the swallowing frequency.

Increasing swallowing frequency is accomplished as a result of reflexing the taste and touch sensory functions of the tongue and the other parts of the mouth and pharynx by stimulating specific cranial nerves to effect responses within certain centers of the primitive brain. These nerves are the trigeminal, facial, glossopharyngeal, vagus, accessory or cranial part and hypoglossal. Of importance is the stimulation of certain cranial nerve reflex actions which are activated to stimulate function of certain muscles and other physiologic functions involving swallowing, snoring, apnea and strengthening muscles of the tongue and throat as well as those muscles under the chin.

The touch aspect is accomplished by the contacting of the dorsum of the tongue by the appliance by a bridge which is a thin expanse of material which is formed of non-toxic plastic commonly used in the dental arts and that spans the distance between the sides of the palatal portion of the appliance. Contact of the bridge with the dorsum of the tongue motivates the tongue to a position such that the apex of the tongue contacts the rugae for achieving the proper proprioceptive sense.

Accordingly, the resulting proper positioning of the tongue encourages proper nasal breathing and the inhibition of air flow over the soft palate. Further advantage is realized by the use of the appliance in that, the glossal and suprahyoid muscles are exercised leading to a reduction of "double chin" phenomena.

It is recognized that snoring and swallowing cannot occur simultaneously. By releasing or dispensing a stimulant for stimulating the swallowing frequency the snoring phenomenon may still further be inhibited. The sensory functions treat the stimulant in the same manner as a bolus of food with the corresponding increase on the swallowing frequency. This is particularly important when other vital activities are at their lowest ebb.

The present invention includes means located on the bridge of the lingual portion of the appliance for dispensing such stimulant. Typical stimulants may be commonly known and commercially available candies such as those sold under the trademark "Life Savers" and the like. Thus, by inducing swallowing by such stimulants the snoring tendency is markedly reduced.

From the malocclusion standpoint correction of muscle dysfunction is the preferred and recommended treatment. Accordingly, the goal is to bring about normal function of those muscles surrounding the dentition that takes part in the masticatory process and deglutition. The treatment in tongue training is to develop proper function of the anterior or tip, corpus, root and related parts of the tongue. For normal swallowing the anterior part of the tongue is behind the upper incisors. The dorsum of the tongue is compressed against the soft palate in contact with the pharynx. Correct positioning of the tongue will thereafter alleviate the symptoms of malocclusion and TMJ and related disorders.

For this class of disorders the appliance should be installed one to two hours prior to sleep to maintain steady conditioning of the tongue for proper positioning. The appliance hereinafter further described in detail encourages the tongue to achieve the aforementioned proper positioning by stimulating the dorsum of the tongue to compress against the soft palate and the interior portion of the tongue against the rugae while swallowing and breathing.

DETAILED DESCRIPTION OF THE INVENTION

Figure 1:
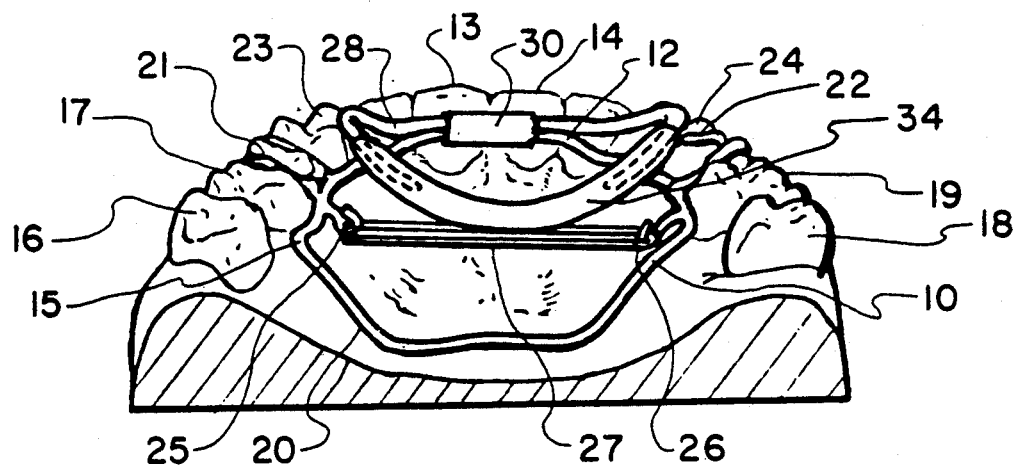
FIG. 1 is a perspective view of the oral appliance in accordance with the invention shown in the installed condition viewed in inverted position.
Figure 2:
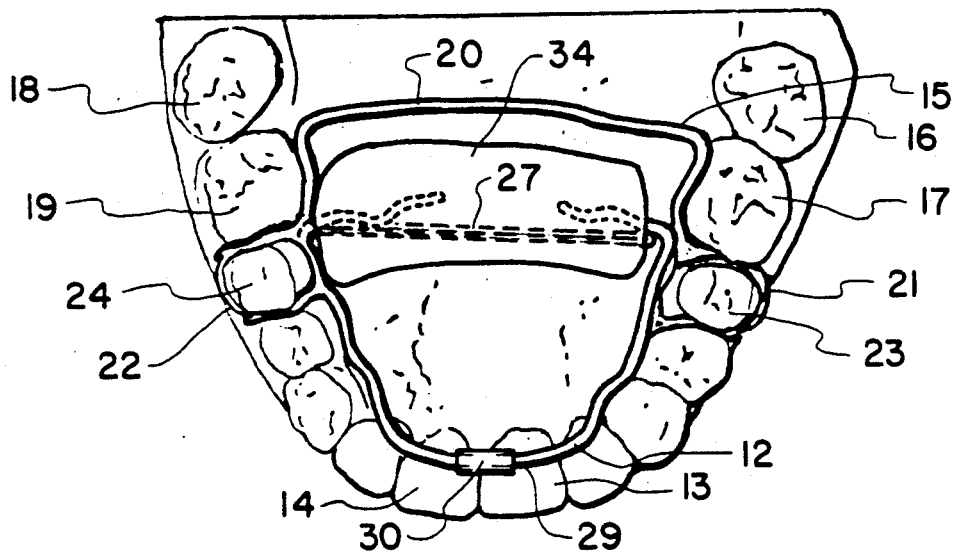
FIG. 2 is a top view of the appliance of FIG. 1.
Figure 3:
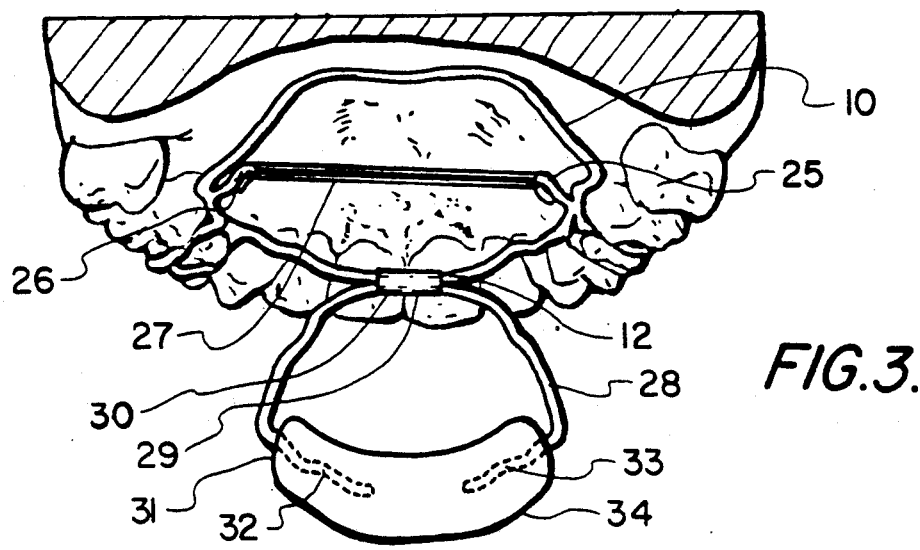
FIG. 3 is an elevation view of the appliance of FIG. 1 with the palatal portion in the open position.

Referring now to FIGS. 1, 2 and 3 the appliance of the present invention includes a palatal portion 10 which is formed of a thin wire filament loop which conforms to and is disposed substantially along the lingual gingival surface of the teeth in the maxillary arch. The palatal portion 10 includes a proximal end 12 which is adjacent the forwardmost teeth 13 and 14 and a distal end 15 which lies adjacent the posterior teeth 16 and 17 on one side of the mouth ,and posterior teeth 18 and 19 located on the other side of the mouth. The rearmost portion 20 of the palatal portion 10 conforms substantially to the contour of the palate with which it comes in contact.

To locate and secure the palatal portion 10, in place, wire clasps 21 and 22 are shaped to conform in encircling relationship to upper teeth 23 and 24 respectively. Selection of the teeth to which wire clasps 21 and 22 are secured depend upon the dental geometry of the person to be fitted with the appliance, and therefore may vary from case to case. Typically the wire clasps 21 and 22 are mounted on either the molar or bicuspids. Selection of these teeth provide maximum leverage advantage and stable anchoring of the palatal portion 10 which diminishes the potential for "rocking motion" while the appliance is installed in the mouth. The manner of looping around the teeth also provides for rapid installation and removal of the appliance with a minimal amount of discomfort.

Depending from palatal portion 10, adjacent to wire clasps 21 and 22, are thin retaining hooks 25 and 26. The retaining hooks 25 and 26 have a somewhat narrow recurving profile which facilitates the holding of a resilient band 27 such as a rubber band or other resilient band means, by and between the hooks. The retaining hooks 25 and 26 extend towards the palate and adjacent the gum region to minimize any interference with the normal movement of the tongue. As will be described later, the resilient band 27 contacts the lingual portion 28 of the appliance and serves to urge the lingual portion away from the palatal portion 10 and towards and in contact with the dorsum of the tongue.

As shown best in FIG. 3 a lingual portion 28, also formed of a thin wire filament loop, is pivotally coupled at its front end 29 by means of hinge 30 to the proximal end 12 of the palatal portion 10. The lingual portion 28 has a rear end 31 having inward pointing tips 32 and 33. The tips 32 and 33 are embedded in a curved bridge 34 which is formed of a nontoxic plastic material. The bridge 34 is in the form of a narrow band that spans the palatal arch and is curved to match the contour of the tongue in the vicinity of the dorsum of the tongue. Although somewhat smaller in overall size than the palatal portion 10, the lingual portion 28 is contoured substantially similar to the palatal portion in the anterior region, having similar reliefs to avoid contact with the upper teeth.

Figure 4:
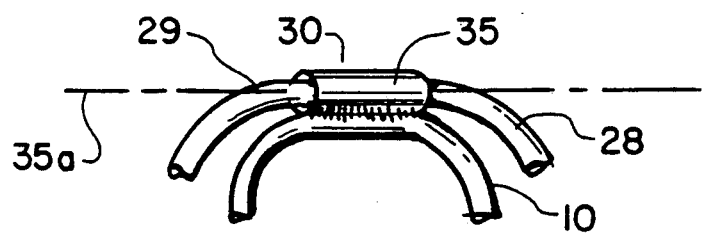
FIG. 4 is a fragmentary perspective view of the appliance of FIG. 1 showing the hinge in greater detail.

The hinge 30 as best shown in FIG. 4 may be a simple structure comprising a small cylindrical tubular receptacle 35 appropriately mounted to the palatal portion 10 through which the front end 29 of lingual portion 28 passes. The length of the tubular receptacle 35 is sized sufficiently to restrict the lingual portion 28 to pivot only about receptacle axis 35A. Although not shown in FIG. 4, axial translation of the lingual portion 28 through the receptacle 35 is prevented by crimping the lingual portion wire filament immediately in the vicinity of the extremities of the receptacle 35. Other methods known in the art may be also used to limit translational movement of the lingual portion 28. Furthermore it is to be understood that the hinge structure is not limited to that disclosed and may be accomplished by other hinging methods known in the art.

As best shown in FIGS. 1 and 3 the lingual retainer 28 is pivotable about pivot axis 35A from an open position (FIG. 3) to a closed position (FIG. 1) where the bridge 34 engages the resilient band 27. Further urging of the bridge 34 against the resilient band 27 results in a reactive force induced in the resilient band 27 to urge the bridge 34 back away from the band. When the appliance is installed in the mouth the aforementioned reactive force feature insures that a desired force will be exerted on the dorsum of the tongue.

When installed the function of the appliance may be described as follows:

The appliance being inserted in the mouth and sufficiently anchored in place, the lingual portion which is in contact with the resilient band presses lightly against the dorsum of the tongue. The mere resting of any light force on the dorsum of the tongue encourages the normal swallowing reflex and causes the proper placement of the body and the anterior parts of the tongue to the hard palate. The free space or void between the hinge 30 and the bridge 34, resulting from the loop geometry of the palatal and lingual portions, provides an unobstructed zone through which the tongue can position itself so that the anterior portion of the tongue contacts the rugae of the palate to achieve the proprioceptive or tactile feel for proper tongue positioning. With the tongue encouraged to be thus positioned against the palate, the passage of air is redirected away from the mouth and the soft palate and through the correct part of the breathing path which is through the nose.

As will be appreciated an important feature of the appliance is the urging effect caused by the resilient band 27. The effects of the tongue, mouth and body movement during sleep are de-emphasized by virtue of the adaptive quality of the resilient band. These normal body movements should not induce discomfort such as choking since the lingual portion 28 is free to pivot about its pivot axis 35A and its proper position will be reestablished during quiescent conditions.

Since the resilient band 27 is easily suspended between the retaining hooks 25 and 26, its attachment and replacement is extremely simple. From a hygiene standpoint, due to the relatively simple construction of the appliance, cleansing, storage and use are also easily accomplished.

Of particular advantage is the simplicity of the appliance and ease of installation. Nevertheless prefabrication procedures are required prior to construction of the appliance. Routine dental impressions are taken of the patient to establish the contour of the lingual gingival surface of the teeth in the maxillary arch area as well as the location of the teeth to which the appliance will be temporarily anchored during appliance use. The appliance is then formed of a non-toxic thin wire filament material the selection of which may be made from a number of materials known in the art. An example of an appropriate metallic material is stainless steel and an example of a plastic material may be nontoxic synthetic resin. The receptacle 35 as well as the wire clasps 21 and 22 may be soldered to the palatal portion 10 by means of dental soldering techniques which are well known in the art.

Figure 5:
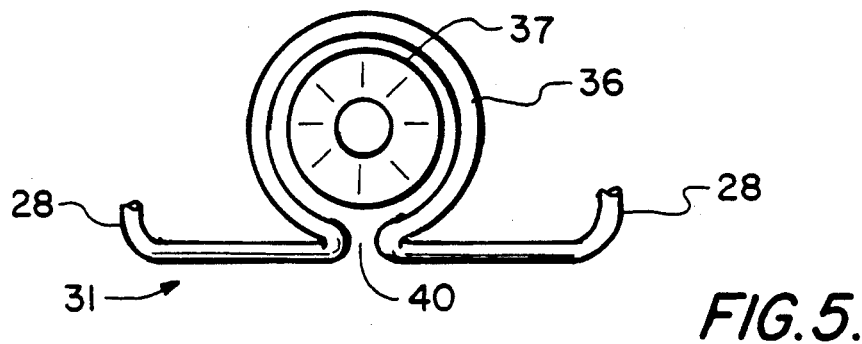
FIG. 5 is a partial top view of an embodiment of the bridge of the appliance of FIG. 1 showing a stimulant tablet held in the bridge.
Figure 6:
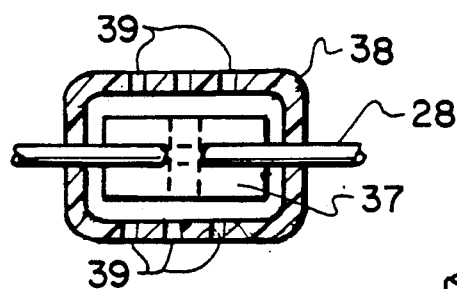
FIG. 6 is a partial fragmentary elevation view of the embodiment of FIG. 5 showing a sleeve over the stimulant tablet.

With reference now to FIGS. 5 and 6 there is shown an alternate embodiment of the bridge 34. The rear end 31 of lingual portion 28 is formed of the wire filament and includes a protruding loop 36. The loop 36 is generally circular having a diameter equal to that of commonly known and available candy or breath mints sold commercially for example under the registered trademark of "Life Savers". The loop 36 lies in a plane essentially parallel to that formed by the portion of the tongue, i.e., the dorsum, with which it is in contact. The candy serves as a stimulant to increase the swallowing frequency. As snoring cannot occur during the swallowing function, the dispensing of a swallowing inducing stimulant will tend to further abate the snoring phenomena.

A removable sleeve 38 (shown in cross-section only in FIG. 6) encases the stimulant 37 while the stimulant is mounted in loop 36. The sleeve 38, formed preferably of a resilient latex material, has a plurality of perforations 39. In normal use, a stimulant 37 is inserted in loop 36 and the latex sleeve is slipped over the loop 36 to maintain the stimulant 37 in place within the loop. Disposed throughout the sleeve 38 are perforations 39 which extend completely through the sleeve wall. Typically the stimulant 37 is soluble, and the perforations and the loop opening 40 provide paths for the entrance of saliva for contact with the stimulant 37 and the dispensing of dissolved stimulant into the throat as a sensitizing taste stimuli. As the stimulant 37 dissolves to a geometry smaller than the diameter of the loop 36 the latex sleeve 38 maintains the diminished stimulant in place until it is completely dissolved and dispensed.

Figure 7:
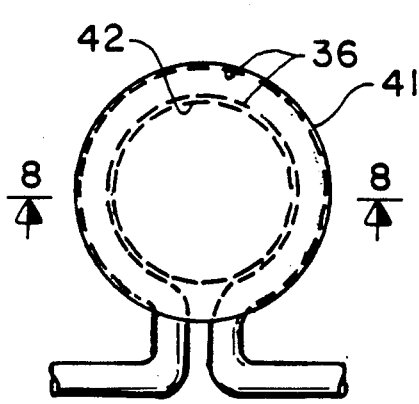
FIG. 7 is a partial top view of an alternate embodiment of the bridge of FIG. 5 showing a liquid stimulant holder.
Figure 8:
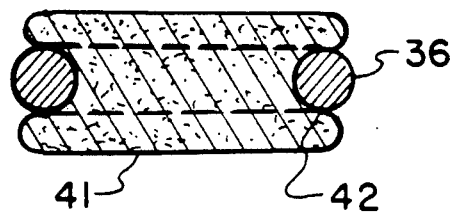
FIG. 8 is a partial elevation cross-sectional view taken along lines 8—8 of FIG. 7.

Alternatively, as shown in FIG. 7 the loop 36 may be fitted with a pliable slightly enlarged absorbent disc 41 in place of the dissolvable stimulant 37. Because the disc has a slightly larger diameter it will be in compression when fitted, and therefore will remain fixed in place in loop 36. Furthermore as shown in the cross-sectional view of FIG. 8, the disc may include a pulley-shaped circumferential groove 42 for holding the disc 41 in mating relationship with the loop 36. A liquid stimulant such as vanilla flavor extract and the like may be applied to the disc which will slowly dispense into the mouth under the normal action of saliva and the contact of the disc on the tongue. In this manner stimulation of the swallowing frequency, similar to that previously described, is accomplished.

Figure 9:
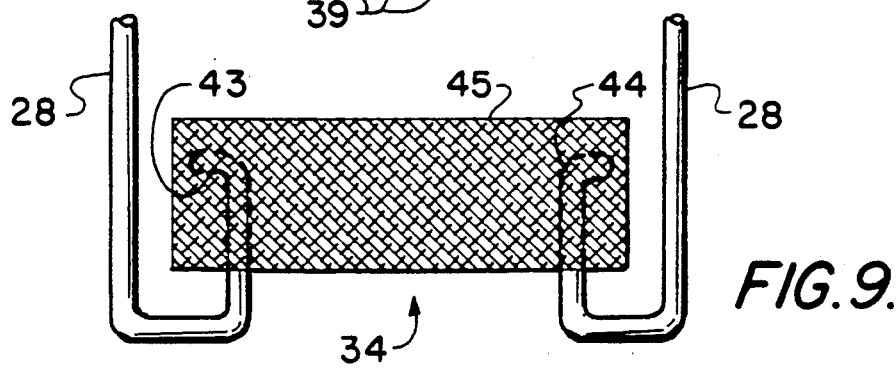
FIG. 9 is an alternate embodiment of the bridge of the appliance of FIG. 1.

Yet another alternate embodiment of the bridge 34 is shown in FIG. 9. The lingual portion 2 includes curled end portion hooks 43 and 44. An absorbent flexible strap 45 is anchored at its ends on the hooks 43 and 44. The strap 45 serves as a bridge previously described with the additional capacity to absorb and dispense a liquid stimulant in a controlled fashion. Mounting the strap 45 in the manner described provides for rapid removal and replacement for hygienic and cleansing considerations. Materials contemplated herein are relatively inexpensive and thus provide a viable alternative to the aforementioned bridge embodiment.

The bridge 34 shown in FIG. 2 may also be adapted to include a stimulant absorbing and dispensing material secured to the bridge either by the use of "Velcro" type fastening, or embedding the material directly into the bridge. Liquid stimulant would then be applied in a manner and fashion previously discussed.

Figure 10:
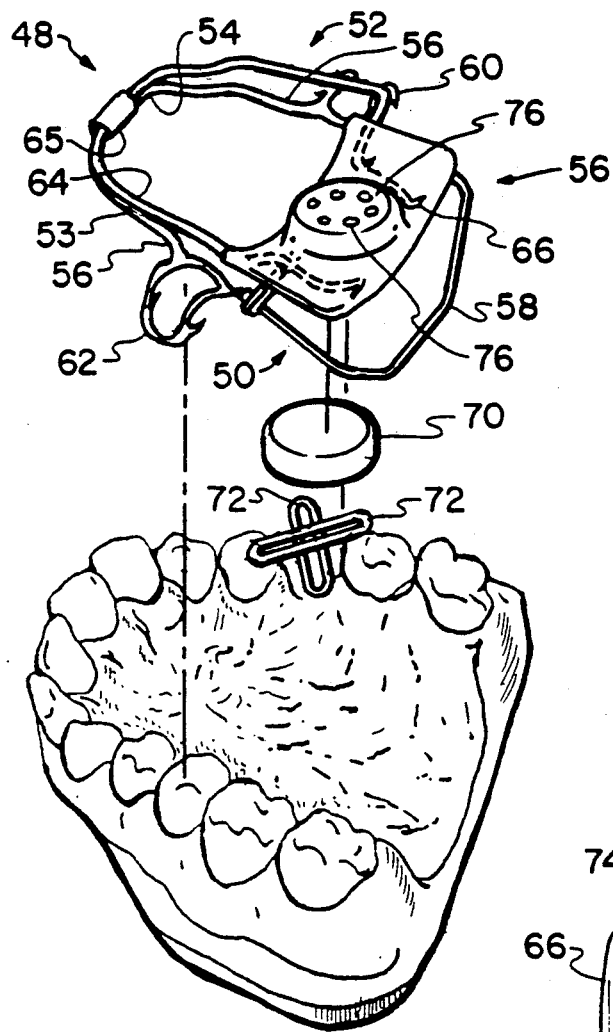
FIG. 10 is a top perspective view of an alternate embodiment of the appliance of FIG. 1.

Referring now to FIG. 10 there is shown another embodiment of an oral appliance of the present invention. Appliance 48 includes a palatal portion 50 and a lingual portion 52. The palatal portion 50 includes a thin wire filament 53 which is shaped to lie along the gingival surface of the upper teeth. In this regard the anterior portion 54 is disposed adjacent the respective central and lateral incisors while the side portions 56 are disposed along the canines and the first and second bicuspids. The posterior portion 58 of the palatal portion 50 is contoured to conform to the profile of the palatal region with which it is in contact.

The palatal portion 50 includes clasps 60 and 62 which are shaped to encircle selected teeth and thereby removably anchor the appliance 48 to such selected teeth in the manner previously described.

Figure 11:
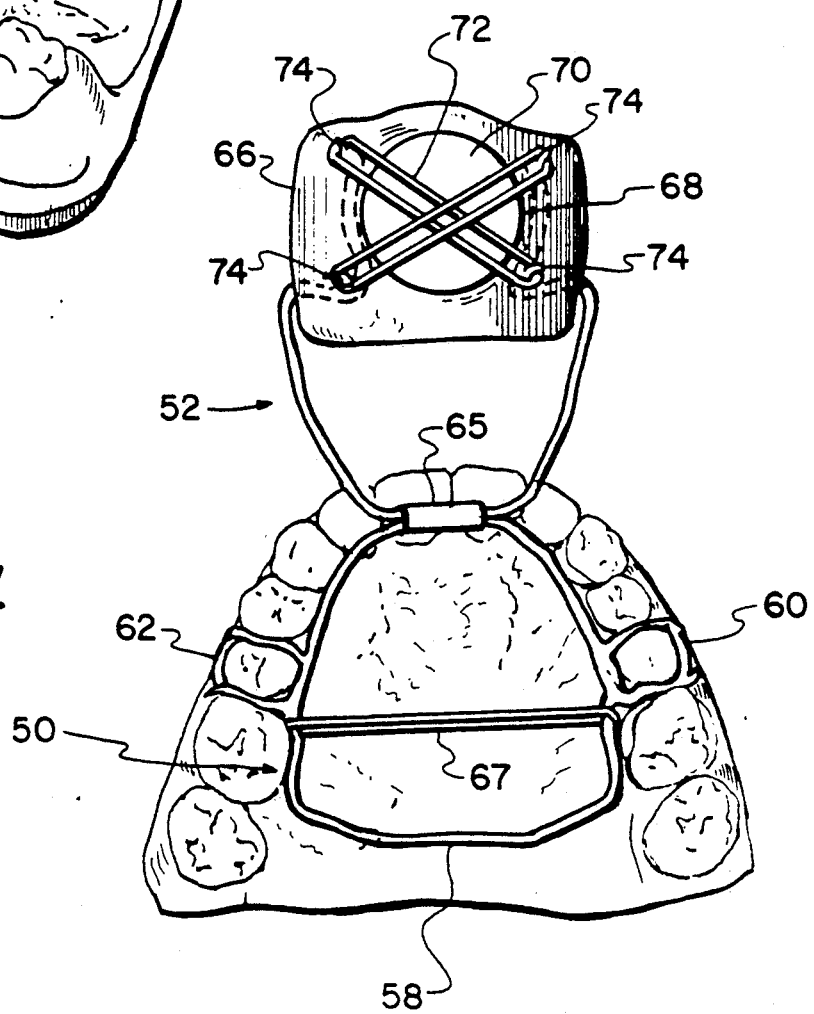
FIG. 11 is a bottom perspective view of the appliance of FIG. 10.

The lingual portion 52 is formed of a U-shaped thin wire filament 64. The lingual portion 52 is pivotally coupled to the palatal portion 50 by means of a hinge 65. Coupled to the ends of the filament 64 is a bridge 66 which is formed of a nontoxic plastic material known in the arts. The bridge 66 is shaped to span the dorsum of the tongue. A recess or receptacle 68 as best shown in FIG. 11 is contoured to receive a solid stimulant tablet 70. An elastic or resilient band 72 such as a rubber band is stretched across the stimulant and the resilient band 72 is fastened in place by means of looping the band 72 around hooks 74 which project from the surface of the bridge. In this manner the tablet 70 is held in place against the bridge until it is completely dissolved under the action of saliva.

The bridge 66 also includes a plurality of apertures 76 which extend completely through the bridge. The apertures 76 provide a path for the flow of saliva to contact the surface of the tablet 70 while providing a path for the discharge of dissolved stimulant.

The bridge 66 is free to pivot about its pivot axis and the contact of the bridge 66, with or without the tablet 70 in place, and thereby encouraging the swallowing frequency. A resilient band 67 stretches across the palatal portion 50 between locations adjacent clasps 60 and 62 so as to contact the bridge 66 and urge it against the dorsum.

As can be understood from FIGS. 10 and 11 when the appliance is installed in the mouth and therefore being in a collapsed condition, the spacing between the bridge 66 and the hinge 65 provides access of the tongue to the rugae. As earlier described contact of the rugae by the tongue is important to achieve the proper proprioceptive feel.

Figure 12:
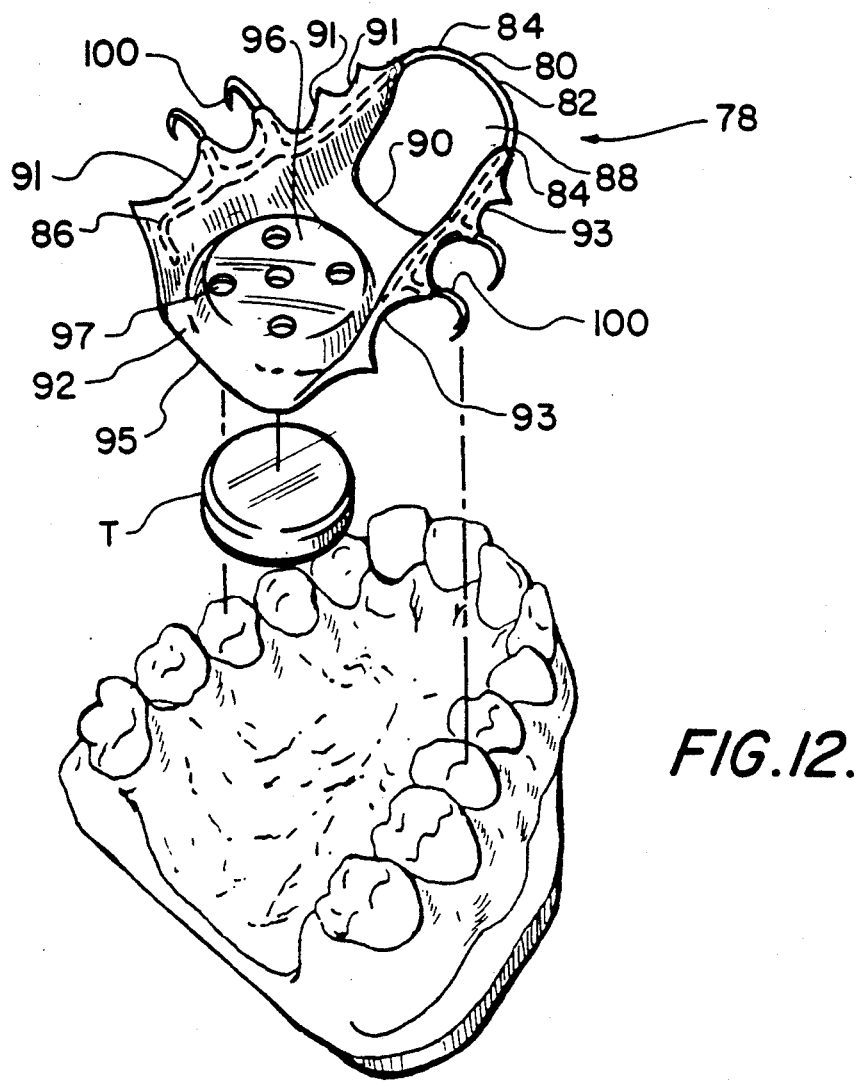
FIG. 12 is a top perspective view of still another alternate embodiment of the present invention.
Figure 13:
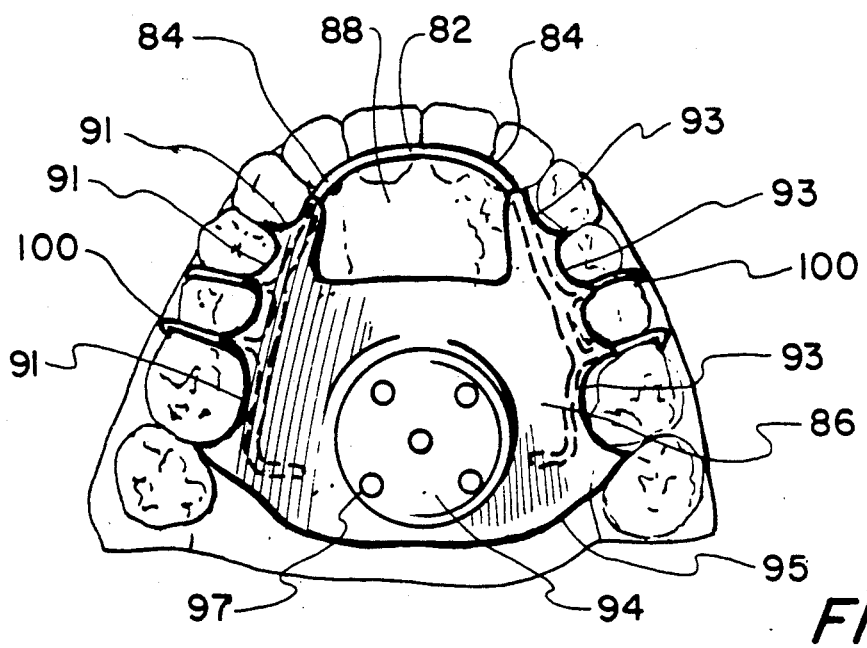
FIG. 13 is a bottom perspective view of the appliance of FIG. 12.

Referring now to FIGS. 12 and 13, there is shown an oral appliance 78 having a thin wire filament 80 which is shaped to lie along the gingival surface of the anterior upper teeth. In this regard, when the appliance is installed, the anterior portion 82 is disposed adjacent to the lingual surface of the central and lateral incisors while the side portions 84 lie along the respective canines and the first and second bicuspids. The filament 80 is embedded in a bridge 86 which is formed of a nontoxic plastic material. The bridge 86 spans the palate and is contoured to conform to the part of the palate with which it is in contact. A void or spacing 88 extends between the side portions 84 from the anterior portion 82 to a station 90 which is about midway the length of the appliance as measured from the anterior portion 82 rearward to the bridge end 92. The spacing provides access to the rugae by the tongue to achieve the proper proprioceptive feel. A series of indentations 91 and 93, conforming in contour of the lingual surfaces of the teeth with which they are in contact, are disposed along respective sides of the bridge 86. A pair of clasps 100 extend outward from the filament 80 which are shaped to grip and removably anchor the appliance to the corresponding teeth in a manner previously described.

The bridge 86 includes a pocket or receptacle 94 formed in the bridge upper side 95, which is substantially cylindrical in cross-section so as to receive a cylindrically shaped stimulant tablet T. Although a cylindrical receptacle is shown it is to be understood that any one of a number of tablet shapes as well as receptacle shapes is contemplated by the invention. The bridge 86 is contoured on its upper side 95 to conform to the profile of the palatal region with which it is in contact. The lower side 96 extends downward sufficiently such that when installed the lowermost surface of the bridge 86 just contacts the dorsum of the tongue. In this manner the bridge 86 serves to both house the stimulant for purposes of increasing the swallowing frequency and to encourage the tongue to the rugae through the spacing 88.

The receptacle 94 includes a plurality of apertures 97 which extend completely through the bridge 86. The apertures 97 provide a path for the flow of saliva to contact the surface of a tablet while providing a path for the discharge of dissolved stimulant.

When the appliance 78 is installed, a tablet or equivalent stimulant dispensing element is confined within the receptacle 94 between the bridge 86 and the palate. Due to the closeness of fit of the bridge 86 to the palate, the stimulant tablet is prevented from movement away from the receptacle and remains essentially in place until completely dissolved.

Figure 14:
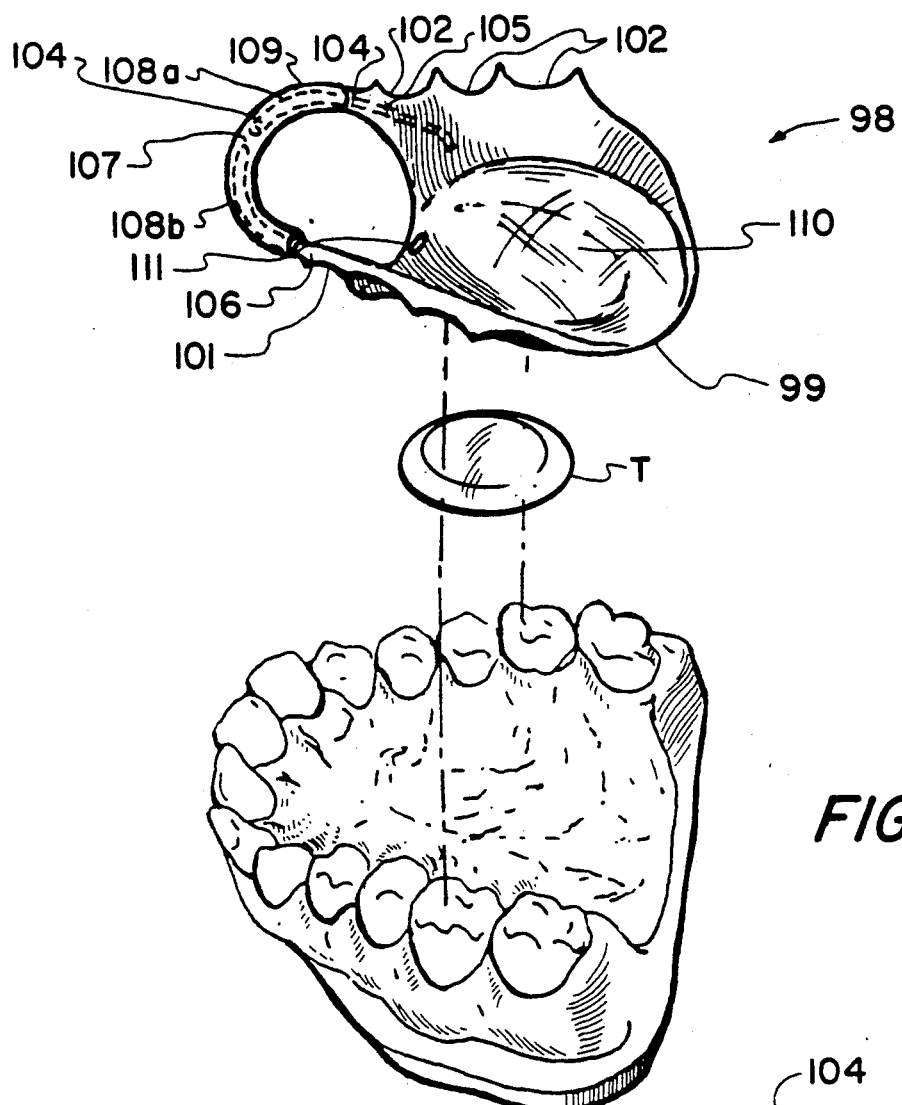
FIG. 14 is a top perspective view of another embodiment of the present invention.
Figure 15:
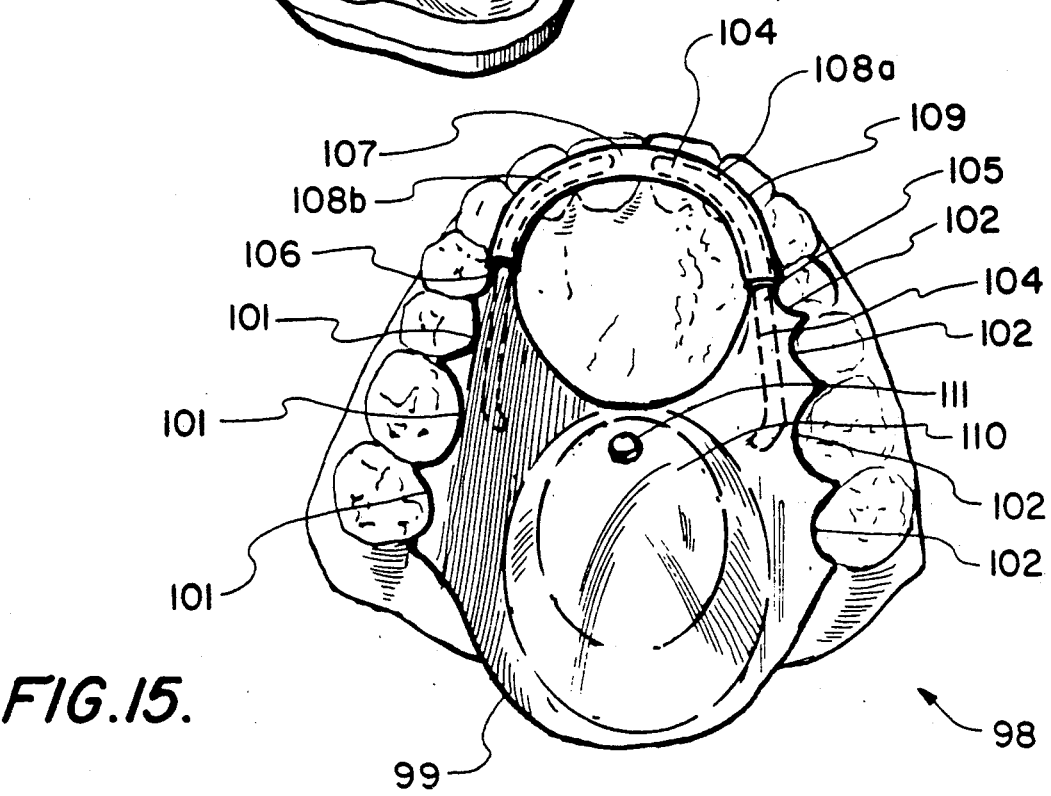
FIG. 15 is a bottom perspective view of the appliance of FIG. 14.

Referring now to FIGS. 14 and 15 there is shown yet still another embodiment of the present invention. Appliance 98 is formed of a single molded unit having a palatal or upper surface 99 which conforms to the contour of the palate of the person intending to use the appliance. Indentations 101 and 102 conform in contour to the teeth with which they are in contact. Although only three indentations per side have been identified it is apparent from FIG. 15 and it is to be understood that the number of indentations may vary, depending upon the geometry of the palate of the particular person intending to use the appliance.

A thin wire filament 104 is embedded within and between appliance tips 105 and 106. As shown in FIGS. 14 and 15 the wire filament 104 is arched between tips 105 and 106 so as to be registrable against the lingual surfaces of the upper anterior teeth. The wire filament 104 is severed at its midpoint 107 to form two individual and discontinuous wire sections 108A and 108B.

Encasing the wire filament 104, is a rubber sleeve 109. The sleeve 109 is formed typically of non-toxic rubber material known in the arts. The rubber sleeve 109 is in contact with the upper front teeth adjacent the gum line. A recess or receptacle 110 for holding a stimulant, is formed in the appliance upper surface 99. A typical stimulant, such as those previously described, and dissolvable under the action of saliva, is inserted in the receptacle 110 prior to installation of the appliance 97 in the mouth. An aperture 111 provides fluid communication between the stimulant in the receptacle 110 and the lingual side of the appliance 97, and thus with the open area of the mouth. The aperture 111 provides for entrance of saliva to contact the stimulant and a passageway for dissolved stimulant to dispense away from the appliance 98.

The appliance 98 is held in place by mucostatic pressure, the action of the tongue to hold the appliance in the palatal position, and the natural clasping action of the indentations 101 and 102 with the corresponding lingual surfaces of the teeth with which they are in contact.

The rubber sleeve 109 serves to provide a cushion for the biting edge of the lower incisors. The cushioning effect minimizes the "jerk reflex" phenomena or the opening of the jaws experienced when the incisal edges of the teeth contact hard metallic or plastic surfaces in the mouth. The sleeve also opens the bite to allow for further eruption of the posterior teeth. This is a decided improvement over the state of the art lower splint which causes intrusion of the posterior teeth caused by the masticatory muscles.

Figure 16:
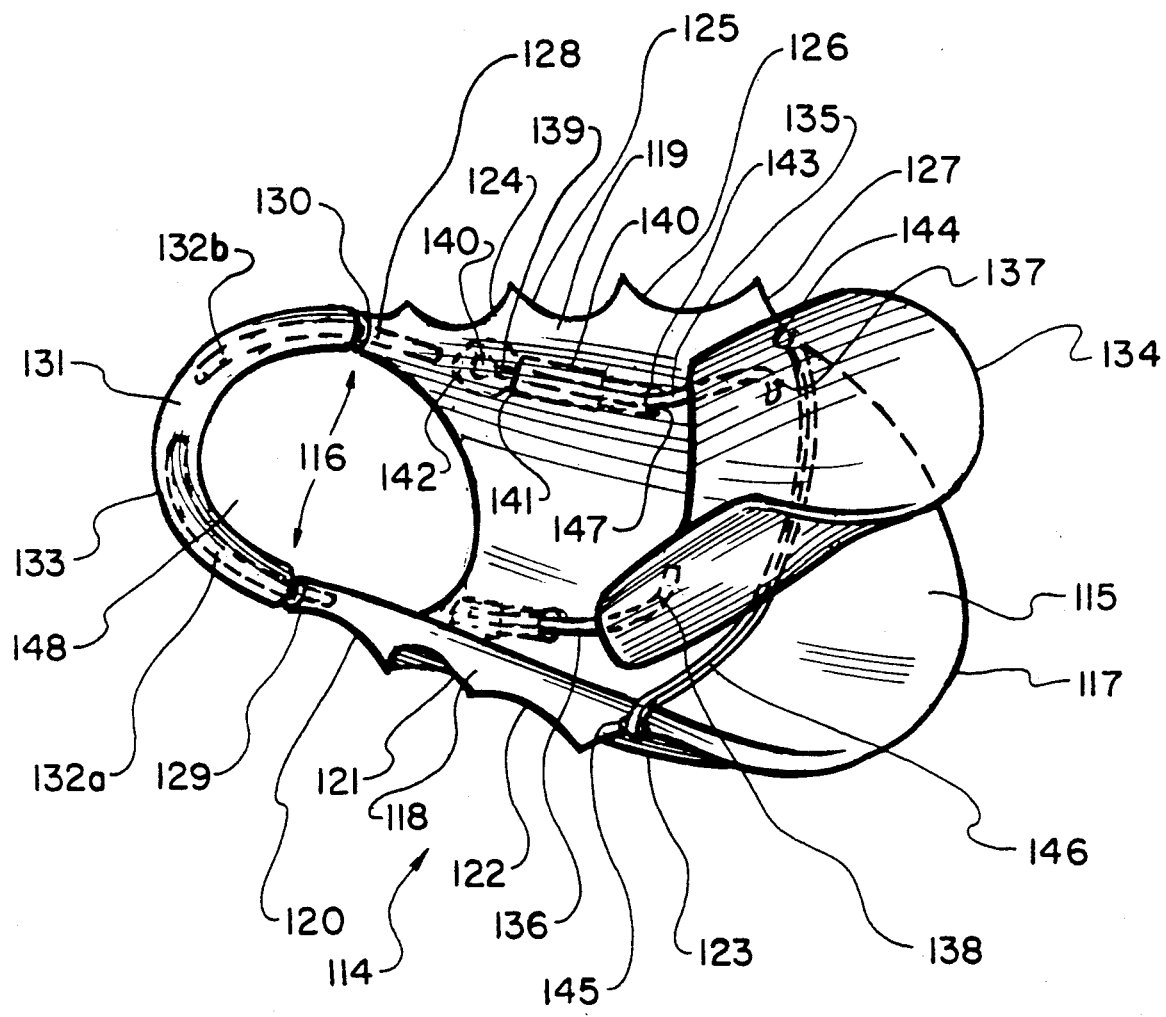
FIG. 16 is a top perspective view of an alternate embodiment of the present invention.

Referring now to FIG. 16 there is shown yet another embodiment of the present invention. Appliance 114 includes a palatal portion 115 having an anterior end 116 and a posterior end 117. Located along either edge of the appliance 114 between the anterior and posterior ends thereof are sides 118 and 119 respectively.

The side 118 includes indentations 120, 121, 122 and 123 and side 119 includes indentations 124, 125, 126 and 127. The indentations conform in contour to the lingual surfaces of the teeth with which they are in contact. When the appliance 114 is to be installed the palatal portion 115 is positioned such that the indentations are aligned with the corresponding teeth with which they match in contour. Slight pressure may be applied to the palatal portion to urge the appliance in place against the respective teeth.

A thin wire filament 128 is embedded within and between appliance tips 129 and 130. The wire filament 128 is arched between tips 129 and 130 so as to be registrable against the lingual surfaces of the upper anterior teeth. The wire filament 128 is severed at its midpoint 131 to form two individual and discontinuous wire sections 132A and 132B. In a manner similar to that for the embodiment of FIG. 14, the individual wire sections provide for slight adaptive movement of the wire filament against lingual surface of the anterior teeth. Moreover the wire sections facilitate the installation and removal of a sleeve over the wire filament.

Encasing the wire filament 128 is a rubber or plastic sleeve 133. The sleeve 133 is formed typically of non-toxic rubber or plastic material known in the arts. When the appliance is installed in the mouth the sleeve 133 is in contact with the upper front teeth at the gum line. The appliance 114 is also held in place by mucostatic pressure and the natural clasping action of the indentations 120 through 127 with the lingual surfaces of the teeth with which they are in contact.

A lingual portion 134 is secured to the palatal portion 115 by means of thin flexible filaments 135 and 136. The filaments may be formed of materials such as nylon filament or others, commonly known in the art. The ends 137 and 138 of the respective filaments are rigidly embedded in the lingual portion 134 whereas the other ends thereof, are capable of limited longitudinal translation within the palatal portion. For purposes of clarity only end 139 is shown in FIG. 16.

More specifically, the filament 135 passes through a small, hollow tubular sleeve 140 which is fixedly embedded within the palatal portion side 119. One end of the filament has an enlarged head 140 which may be formed by a crimping technique or by melting the filament to form a bead. The size of the head 140 is greater than the diameter of the sleeve 139 so that movement of the filament out of the palatal portion stops when the head 140 abuts against sleeve end 141. There is sufficient clearance 142 within the palatal portion to permit movement of the filament longitudinally and reciprocally through the sleeve.

The filament 135 exits from the palatal portion through bore 143. The bore 143 extends from the sleeve 139 to the surface of the palatal portion and is of a diameter slightly larger than that of the filament 135. As will be discussed below, the location of the bore 143 at the surface of the palatal portion is the point about which the lingual portion pivots.

As previously discussed the other end 137 of the filament 135 is fixedly embedded within the lingual portion 134. The range of movement of the filament is limited by the contact of the head 140 against the sleeve end 141 in the outward direction and by the contact of the lingual portion 134 and the palatal portion 115 in the inward direction.

Stretched across the palatal portion 115 from anchors 144 and 145 is a resilient rubber band 146. The rubber band 146 is in contact with the lingual portion 134 and urges it about the pivot point 147 away from the palatal portion 115.

The lingual portion 134 is in the form of a narrow bridge that when the appliance is installed in the mouth, spans the dorsum of the tongue (to which it conforms in shape in the area of contact) and is for contacting the tongue against the action of the rubber band 146. As has been previously described for the other embodiments, contact of the lingual portion 134 with the dorsum urges the tongue through central spacing 148 and to the rugae for proper proprioceptive feel.

Although the coupling of the lingual portion 134 to the palatal portion 115 has been described by means of thin flexible filament 135, it is to be understood that filament 136 is coupled to the lingual and palatal portions at side 118 in a similar fashion as is filament 135. Furthermore, although not shown in detail in FIG. 16, it is to be understood that the lingual portion 134 may contain means for dispensing a swallowing frequency inducing stimulant as heretofore described in great detail.

Additionally, although the location of the bore 143 at the surface of the palatal portion (at pivot point 147) is shown in FIG. 16 to be adjacent to the bicuspid area, when the appliance is installed, it is to be understood that the location of the pivot point 147 may vary along the palatal portion side 119 according to the user's particular dental geometry. Accordingly, the pivot point 147 may be located from between the cuspid area to the molar area.

What is claimed is:

1. An oral appliance for tongue thrust correction comprising a pair of thin wire filament loops pivotally coupled together for limited pivotal movement about a pivot axis, one loop forming a palatal portion including clasp means for anchoring the palatal portion to corresponding selected ones of the upper teeth, the other loop forming a lingual portion including bridge means for spanning the dorsum of the tongue, and spring means for urging the bridge means away from the palatal portion and against the dorsum wherein contact with the dorsum encourages the tongue to a position through the palatal and lingual portions and to seat on the rugae for maintaining proper proprioceptive sense.

2. The oral appliance of claim 1 wherein the bridge means includes means for holding and dispensing a stimulant for stimulating the swallowing frequency.

3. The oral appliance of claim 2 wherein the dispensing means comprises loop means formed in the bridge means and adapted to receive a dissolvable stimulant.

4. The oral appliance of claim 3 including cover means for substantially encasing the stimulant received by the loop means, the cover means having at least one perforation for admitting saliva and dispensing dissolved stimulant.

5. The oral appliance of claim 2 wherein the dispensing means includes absorption means for absorbing and then dispensing a liquid stimulant.

6. The oral appliance of claim 5 wherein the dispensing means comprises liquid absorbing elastic material secured to the bridge means.

7. The oral appliance of claim 1 wherein the spring means comprises a resilient band mounted laterally across the palatal portion for contact with the bridge means.

8. An oral appliance for tongue thrust correction comprising:

a palatal portion having proximal and distal ends, the palatal portion formed of thin wire filament disposed along a lingual gingival surface of the upper teeth, the proximal end being adjacent the anterior teeth and the distal end being adjacent the posterior teeth;

a lingual portion comprising a thin wire filament having first and second ends, the lingual portion being pivotally mounted at its first end to the proximal end of the palatal portion for movement about a pivot axis;

bridge means, secured to the second end, substantially spanning the palate for bearing against the dorsum of the tongue; and resilient band means connected laterally across the distal end of the palatal portion for urging the lingual portion away from the palatal portion and the bridge means against the dorsum of the tongue.

9. The oral appliance of claim 8 wherein the bridge means comprises a thin arched band whose arc substantially conforms to the contour of the dorsum of the tongue.

10. The oral appliance of claim 9 wherein the resilient band means biases the bridge means against the dorsum of the tongue sufficiently to cause the tongue to contact the rugae for proper proprioceptive feel.

11. The oral appliance of claim 10 wherein the bridge means is formed of a nontoxic plastic material.

12. The oral appliance of claim 10 wherein the palatal portion includes a pair of clasps, each clasp adapted for detachable securement to respective and similarly located teeth on respective sides of the mouth.

13. The oral appliance of claim 12 wherein the similarly located tooth is a molar.

14. The oral appliance of claim 13 wherein the wire filament is disposed along a lingual gingival surface of teeth in the maxillary arch.

15. The oral appliance of claim 8 wherein the bridge means includes means for dispensing a stimulant for stimulating and increasing the swallowing frequency.

16. The oral appliance of claim 15 wherein the bridge means comprises a thin wire filament having protruding loop means located intermediate the first and second ends, the loop means adapted to receive a stimulant and cover means to substantially encase the stimulant within the loop means, the cover means having at least one perforation for admitting saliva and dispensing the stimulant.

17. The oral appliance of claim 16 wherein the stimulant is soluble and the cover means is formed of thin latex having a plurality of perforations for aiding the dissolving of the stimulant under the action of saliva, and dispensing the dissolved stimulant.

18. The oral appliance of claim 15 wherein the dispensing means includes absorption means for absorbing and then dispensing liquid stimulant.

19. The oral appliance of claim 18 wherein the dispensing means comprises liquid absorbing elastic secured to the bridge means.

20. An improved oral appliance for correcting tongue thrust, the improvement comprising, a palatal portion formed of a thin wire filament loop having proximal and distal ends, the palatal portion secured to selected ones of the upper teeth, a lingual portion formed of thin wire filament loop having first and second ends, the lingual portion pivotally mounted at its first end to the proximal end of the palatal portion for limited pivotal motion therebetween, bridge means mounted at the second end of the lingual portion for spanning the dorsum of the tongue and means for urging the bridge means against the dorsum of the tongue.

21. An oral appliance comprising a thin wire filament having anterior and posterior portions, the filament disposed along a lingual gingival surface of the upper teeth, the filament including clasp means for anchoring the appliance to corresponding selected ones of the upper teeth, bridge means coupled to the posterior portion of the filament, the bridge means spanning across a palatal region of the mouth, the bridge means including receptacle means for receiving a stimulant and maintaining said stimulant between the bridge means and the palate.

22. The oral appliance of claim 21 wherein the bridge means includes at least one aperture for admitting saliva and dispensing the stimulant.

23. An oral appliance comprising a pair of thin wire filament loops pivotally coupled together for limited pivotal movement about a pivot axis, one loop forming a palatal portion including clasp means for anchoring the palatal portion to corresponding selected ones of the upper posterior teeth, the other loop forming a lingual portion including bridge means spanning the dorsum of the tongue, the bridge means including means for dispensing a stimulant for stimulating the swallowing frequency.

24. The oral appliance of claim 23 wherein the means for dispensing comprises a receptacle formed in the bridge means for receiving the stimulant and means for maintaining the stimulant within the receptacle.

25. The oral appliance of claim 24 wherein the stimulant is in tablet form being dissolvable under the action of saliva and the receptacle includes at least one aperture for admitting saliva and dispensing dissolved stimulant.

26. The oral appliance of claim 25 wherein the means for maintaining the stimulant within the receptacle comprises elastic means coupled to and extending across the receptacle and over the stimulant thereby urging the stimulant against the bridge means.

27. An oral appliance comprising a molded palatal portion having anterior and posterior portions, the palatal portion having sides extending between the anterior and posterior portions and conforming to the contour of the surface of the teeth with which respective sides are in contact, said palatal portion having a lingual side and an underside for contacting the palate, the underside conforming to the contour of the palate, the underside including receptacle means for receiving a stimulant and maintaining said stimulant between the underside and the palate, at least one aperture extending completely through the receptacle means for providing fluid communication between the receptacle means and the lingual side and a thin wire filament arched between the sides at the anterior portion and registrable against lingual surfaces of the upper anterior teeth, and a rubber sleeve encasing the filament along the length thereof.

28. The oral appliance of claim 27 wherein the wire filament is severed to form two discrete discontinuous segments.

* * * * *